United States Patent
Greenspan et al.

(10) Patent No.: US 9,122,955 B2
(45) Date of Patent: Sep. 1, 2015

(54) METHOD AND SYSTEM OF CLASSIFYING MEDICAL IMAGES

(75) Inventors: Hayit Greenspan, Kfar-Bilu (IL); Jacob Goldberger, Tel-Aviv (IL); Uri Avni, Tel-Aviv (IL); Eli Konen, Tel-Aviv (IL); Michal Sharon, Moshav Ganei-Yochanan (IL)

(73) Assignees: Ramot at Tel-Aviv University Ltd., Tel-Aviv (IL); Tel HaShomer Medical Research Infrastructure and Services Ltd., Ramat-Gan (IL); Bar-Ilan University, Ramat-Gan (IL)

( * ) Notice: Subject to any disclaimer, the term of this patent is extended or adjusted under 35 U.S.C. 154(b) by 21 days.

(21) Appl. No.: 13/170,200

(22) Filed: Jun. 28, 2011

(65) Prior Publication Data

US 2011/0317892 A1  Dec. 29, 2011

Related U.S. Application Data

(60) Provisional application No. 61/358,979, filed on Jun. 28, 2010.

(51) Int. Cl.
G06K 9/46 (2006.01)
G06F 17/30 (2006.01)

(52) U.S. Cl.
CPC .......... G06K 9/4676 (2013.01); G06F 17/3028 (2013.01); G06F 17/30268 (2013.01)

(58) Field of Classification Search
None
See application file for complete search history.

(56) References Cited

U.S. PATENT DOCUMENTS

| | | | |
|---|---|---|---|
| 7,738,683 B2 * | 6/2010 | Cahill et al. | 382/128 |
| 7,751,984 B2 * | 7/2010 | Tang | 702/19 |
| 8,208,697 B2 * | 6/2012 | Schaffer et al. | 382/128 |
| 8,407,267 B2 * | 3/2013 | Feulner et al. | 382/131 |
| 2003/0195897 A1 * | 10/2003 | Agrafiotis et al. | 707/101 |
| 2004/0165767 A1 * | 8/2004 | Gokturk et al. | 382/159 |
| 2005/0102246 A1 * | 5/2005 | Movellan et al. | 706/12 |
| 2005/0286767 A1 * | 12/2005 | Hager et al. | 382/190 |
| 2006/0104494 A1 * | 5/2006 | Collins et al. | 382/128 |
| 2006/0115146 A1 * | 6/2006 | Ogura et al. | 382/159 |
| 2006/0257027 A1 * | 11/2006 | Hero et al. | 382/190 |
| 2007/0025606 A1 * | 2/2007 | Gholap et al. | 382/128 |
| 2007/0036402 A1 * | 2/2007 | Cahill et al. | 382/128 |
| 2007/0165932 A1 * | 7/2007 | Nishimura et al. | 382/128 |
| 2007/0189602 A1 * | 8/2007 | Rao et al. | 382/159 |
| 2007/0217676 A1 * | 9/2007 | Grauman et al. | 382/170 |
| 2007/0237355 A1 * | 10/2007 | Song et al. | 382/100 |

(Continued)

OTHER PUBLICATIONS

Caicedo, Juan, Angel Cruz, and Fabio González. "Histopathology image classification using bag of features and kernel functions." Artificial Intelligence in Medicine (2009): 126-135.*

(Continued)

*Primary Examiner* — Stephen R Koziol
*Assistant Examiner* — Sean Conner

(57) ABSTRACT

A method of generating a category model for classifying medical images. The method comprises providing a plurality of medical images each categorized as one of a plurality of categorized groups, generating an index of a plurality of visual words according to a distribution of a plurality of local descriptors in each the image, modeling a category model mapping a relation between each visual word and at least one of the categorized groups according to the index, and outputting the category model for facilitating the categorization of an image based on local descriptors thereof.

17 Claims, 5 Drawing Sheets
(2 of 5 Drawing Sheet(s) Filed in Color)

(56) References Cited

U.S. PATENT DOCUMENTS

| | | | |
|---|---|---|---|
| 2008/0002856 A1* | 1/2008 | Ma et al. | 382/103 |
| 2008/0273752 A1* | 11/2008 | Zhu et al. | 382/103 |
| 2009/0060351 A1* | 3/2009 | Li et al. | 382/224 |
| 2009/0080731 A1* | 3/2009 | Krishnapuram et al. | 382/128 |
| 2009/0080732 A1* | 3/2009 | Zhou et al. | 382/128 |
| 2009/0092282 A1* | 4/2009 | Avidan et al. | 382/103 |
| 2009/0116716 A1* | 5/2009 | Zhou | 382/131 |
| 2009/0169075 A1* | 7/2009 | Ishida et al. | 382/128 |
| 2009/0310836 A1* | 12/2009 | Krishnan et al. | 382/128 |
| 2009/0318815 A1* | 12/2009 | Barnes et al. | 600/473 |
| 2010/0097455 A1* | 4/2010 | Zhang et al. | 348/119 |
| 2010/0177943 A1* | 7/2010 | Zhao et al. | 382/131 |
| 2010/0177950 A1* | 7/2010 | Donovan et al. | 382/133 |
| 2010/0220906 A1* | 9/2010 | Abramoff et al. | 382/130 |
| 2010/0328452 A1* | 12/2010 | Jung et al. | 348/135 |
| 2010/0329529 A1* | 12/2010 | Feldman et al. | 382/131 |
| 2011/0299782 A1* | 12/2011 | Hamsici et al. | 382/195 |
| 2012/0147176 A1* | 6/2012 | Zhang et al. | 348/118 |
| 2012/0213443 A1* | 8/2012 | Shin et al. | 382/190 |
| 2012/0219211 A1* | 8/2012 | Ding et al. | 382/159 |

OTHER PUBLICATIONS

Deselaers, Thomas, and Thomas Deserno. "Medical image annotation in ImageCLEF 2008." Evaluating Systems for Multilingual and Multimodal Information Access (2009): 523-530.*

Zhou, Xiang Sean, and Thomas S. Huang. "Unifying keywords and visual contents in image retrieval." Multimedia, IEEE 9.2 (2002): 23-33.*

Cao, Yang, et al. "Spatial-bag-of-features." Computer Vision and Pattern Recognition (CVPR), 2010 IEEE Conference on. IEEE, 2010.*

Feulner, Johannes, et al. "Estimating the body portion of CT volumes by matching histograms of visual words." SPIE Medical Imaging. International Society for Optics and Photonics, 2009.*

Morioka, Nobuyuki, and Shin'ichi Satoh. "Building compact local pairwise codebook with joint feature space clustering." Computer Vision—ECCV 2010. Springer Berlin Heidelberg, 2010. 692-705.*

Philbin, James, et al. "Object retrieval with large vocabularies and fast spatial matching." Computer Vision and Pattern Recognition, 2007. CVPR'07. IEEE Conference on. IEEE, 2007.*

Avni et al. "X-Ray Image Categorization and Retrieval Using Patch-Based Visual Words Representation", Proceedings of the Sixth IEEE International Symposium on Biomedical Imaging: From Nano to Macro (ISBI), Boston, Massachusetts, USA, Jul. 3-6, 2009, p. 350-353, 2009.

Deselaers et al. "Bag-of-Visual-Words Models for Adult Image Classification and Filtering", International Conference on Pattern Recognition, ICPR, 4 P., 2008.

Weizman et al. "Detection of Urban Zones in Satellite Images Using Visual Words", IEEE International Geoscience and Remote Sensing Letters, 2 P., 2008.

Yang et al. "Evaluating Bag-of-Visual-Words Representations in Scene Classification", International Multimedia Conference: Proceedings of the International Workshop on Workshop on Multimedia Information Retrieval , Augsburg, Bavaria, Germany, Sep. 24-29, 2007, p. 197-206, 2007.

* cited by examiner

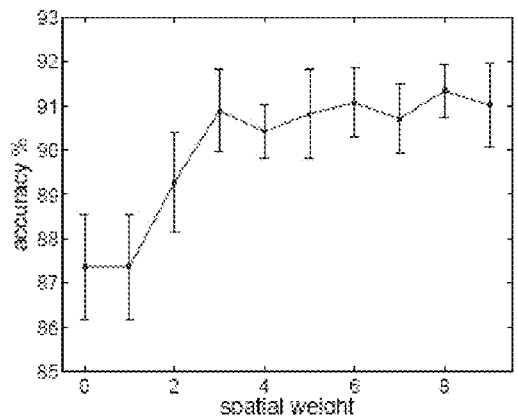
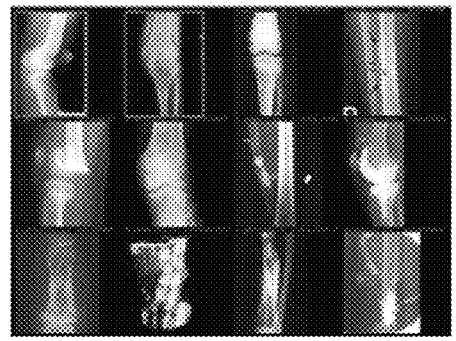
FIG. 5　　　　　　　　FIG. 6
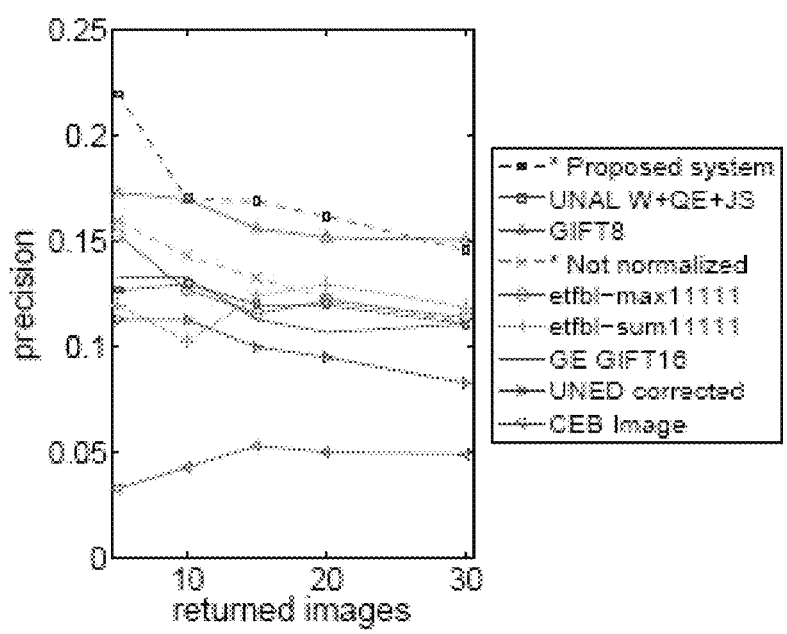
FIG. 7

METHOD AND SYSTEM OF CLASSIFYING MEDICAL IMAGES

RELATED APPLICATION

This application claims the benefit of priority under 35 USC 119(e) of U.S. Provisional Patent Application No. 61/358,979 filed Jun. 28, 2010, the contents of which are incorporated herein by reference in their entirety.

FIELD AND BACKGROUND OF THE INVENTION

The present invention relates to analysis of medical images and, more particularly, but not exclusively to automatic analysis and classification of medical images depicting an organ or a human body system.

Systems and devices for visualizing the inside of living organisms are among the most important medical developments in the last thirty years. Systems like X-ray scanners, computerized tomography (CT) scanners and magnetic resonance imaging (MRI) scanners allow physicians to examine internal organs or areas of the body that require a thorough examination. In use, the visualizing scanner outputs a medical image, such as a cross-sectional image, or a sequence of computerized cross-sectional images of a certain body organ, which is then diagnosed by radiologists and/or other physicians.

In most hospitals and radiology centers, the medical images are transferred to a picture archiving communication system (PACS) before being accessed by the radiologists. The PACS is installed on one or more of computers, which are dedicated for storing, retrieving, distributing and presenting the stored 3D medical images. The 3D medical images are stored in an independent format. The most common format for image storage is digital imaging and communications in medicine (DICOM).

The rapid growth of computerized medical imagery using PACS in hospitals throughout the world led to the development of systems for classifying visual medical data. For example, International Patent Application Publication No. WO/2007/099525, filed in Feb. 18, 2007 describes a system for analyzing a source medical image of a body organ. The system comprises an input unit for obtaining the source medical image having three dimensions or more, a feature extraction unit that is designed for obtaining a number of features of the body organ from the source medical image, and a classification unit that is designed for estimating a priority level according to the features.

Another example is described in U.S. Pat. No. 6,754,675 filed on Jul. 16, 2001 which describes image retrieval system contains a database with a large number of images. The system retrieves images from the database that are similar to a query image entered by the user. The images in the database are grouped in clusters according to a similarity criterion so that mutually similar images reside in the same cluster. Each cluster has a cluster center which is representative for the images in it. A first step of the search to similar images selects the clusters that may contain images similar with the query image, by comparing the query image with the cluster centers of all clusters. A second step of the search compares the images in the selected clusters with the query image in order to determine their similarity with the query image.

SUMMARY OF THE INVENTION

According to some embodiments of the present invention there is provided a method of generating a category model for classifying medical images. The method comprises providing a plurality of medical images each categorized as one of a plurality of categorized groups, generating an index of a plurality of visual words according to a distribution of a plurality of local descriptors in each the image, modeling a category model mapping a relation between each the visual word and at least one of the plurality of categorized groups according to the index, and outputting the category model for facilitating the categorization of an image based on local descriptors thereof.

Optionally, the method further comprises dividing the plurality of medical images among the plurality of categorized groups.

Optionally, the index comprises less than 700 visual words.

Optionally, the plurality of medical images are part of a training set having more than 10,000 medical images.

Optionally, the generating comprises clustering the plurality of local descriptors in a plurality of clusters, the plurality of visual words being defined according to the plurality of clusters.

More optionally, the clustering is performed according to a principal component analysis (PCA).

Optionally, the modeling is performed using a support vector machine (SVM) training procedure.

Optionally, the SVM training procedure is a multi-class SVM with a radial basis function (RBF) kernel.

Optionally, the plurality of medical images are provided from a picture archiving communication system (PACS).

Optionally, the plurality of categorized groups define a plurality of pathologies.

Optionally, the method further comprises automatically categorizing the plurality of medical images.

According to some embodiments of the present invention there is provided a method of classifying a medical image using a category model. The method comprises providing a category model which maps a plurality of visual-words in a space, each the visual-word being associated with at least one of a plurality of image categories, receiving an examined medical image, identifying a group of the plurality of visual-words in the examined medical image, using the category model to match the group with an image category of the plurality of image categories, and outputting the image category.

Optionally, the outputting comprises presenting the image category in a client terminal used to provide the examined medical image.

Optionally, identifying is performed without segmenting the examined medical image.

Optionally, identifying is performed without registering the examined medical image.

More optionally, the method further comprises updating the category model according to the matching.

According to some embodiments of the present invention there is provided a medical image analysis system of classifying a medical image using a category model. The system comprises a repository which stores a category model mapping a plurality of visual-words in a space, each the visual-word being associated with at least one of a plurality of image categories, an input unit which receives an examined medical image, a categorization module which identifies a group of the plurality of visual-words in the examined medical image and uses the category model to match the group with an image category of the plurality of image categories, and a presentation unit which present the image category in response to the receiving of the examined medical image.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart of a method of generating a category model for classifying medical images, according to some embodiments of the present invention;

FIG. 2 is a method of classifying a medical image using a category model, for example as generated according to FIG. 1, according to some embodiments of the present invention;

FIG. 3 is a schematic illustration of a medical image analysis system of classifying a medical image using a category model, for example as generated according to FIG. 1, according to some embodiments of the present invention;

FIG. 4A is a distribution images across categories;

FIG. 4B depicts a graph which illustrates the effect of dictionary size on the accuracy of categorization using a category model generated as depicted in FIG. 2, according to some embodiments of the present invention;

FIG. 4C depicts a graph which illustrates the effect of dictionary size on the accuracy of categorization when the image patches have between 5 and 8 feature components, according to some embodiments of the present invention;

FIG. 5 is a graph mapping the relation between the weight of spatial features in x-axis and the classification accuracy in y-axis where the bars show mean and standard deviation of 20 experiments;

FIG. 6 is a set of images where the first two images are the query images and the following images (left to right, top to bottom) are the retrieval results; and FIG. 7 is a graph depicting the relation between the precision shown for first 5, 10, 15, 20 and 30 returned images and the number of images.

DESCRIPTION OF EMBODIMENTS OF THE INVENTION

Figure 1:
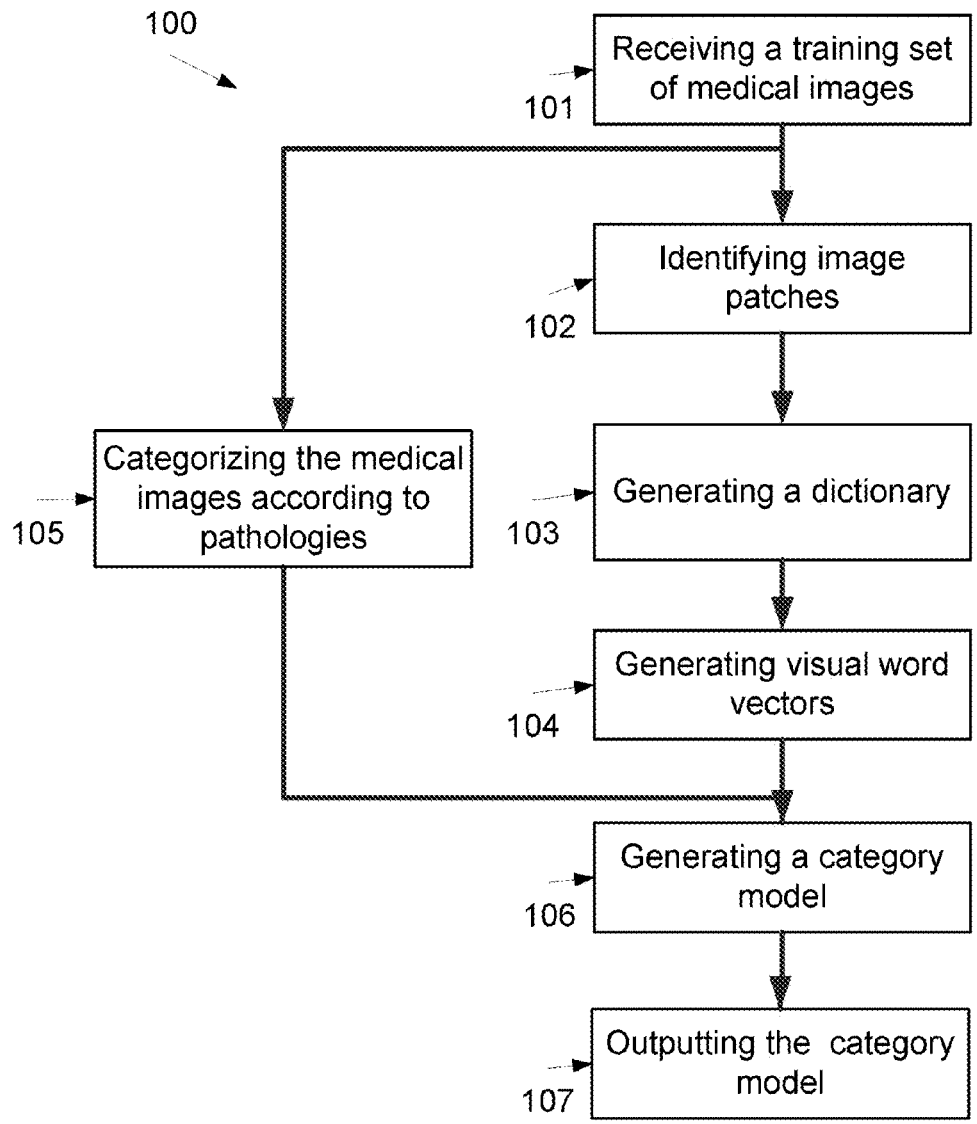

The present invention relates to analysis of medical images and, more particularly, but not exclusively to automatic analysis and classification of medical images depicting an organ or a human body system.

According to some embodiments of the present invention there are provided systems and methods of modeling a category model which is used for classifying medical images. The method is based on an analysis of a plurality of medical images, such as X-ray scans and volumetric scan images. Each medical image is categorized, manually and/or automatically, as one of a plurality of categorized groups, for example according to visual characteristic of one or more pathologies. This allows generating an index, a dictionary, of visual words, which are patterns of salient local image patches. The dictionary is generated according to a distribution of a plurality of local descriptors in each image. Now, a category model mapping a relation between each visual word and one or more of the plurality of categorized groups is modeled according to the index. In such a manner, the category model may be provided, for example sent, for facilitating the categorization of an image based on local descriptors thereof.

According to some embodiments of the present invention there are provided systems and methods of classifying a medical image using a category model, such as the category model which is outlined above and described below. This method is based on a category model which maps a plurality of visual-words in a space where each visual-word is associated with one or more image categories. The category model may be locally stored in a computing unit that implements the method or in a remote and/or external database. Now, an examined medical image is received and a group of visual-words which are documented in the category model are extracted from the examined medical image, optionally using an index of visual words, such as the aforementioned dictionary. This allows using the category model to match the group with an image category of the plurality of image categories and outputting the image category.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a flowchart of a method of generating a category model for classifying medical images, according to some embodiments of the present invention.

First, as shown at 101 a training set having a plurality of medical images is received. As used herein, a medical image means an X-Ray scan image, a computerized tomography (CT) scan image, a magnetic resonance imager (MRI) scan image, and a positron emission tomography (PET)-CT scan image. For example, the images are taken from a medical database, such as PACS or radiology information system (RIS). Optionally, the number of medical images in the training set is between few hundreds to few hundreds of thousands or even more. For example, the training set includes about 1200 medical images or about 65,000 medical images as exemplified below. Optionally, the number images changes according to the number of possible pathologies which are categorized in the category model. Optionally a ratio of about 2000 images per category is maintained.

Now, as shown at 102, local descriptors, which may be referred to herein as image patches, are identified in each one of the provided medical images. The local descriptors are repeatable multidimensional features so that if there is a transformation between two instances of an object, corresponding points are detected and substantially identical descriptor values are obtained around each. Optionally each image patch is represented by a multidimensional record.

Optionally, the descriptors are resistant to geometric and illumination variations, for example as described in any of the following T. Lindenberg, Scale-space theory in computer vision, Kluwer Academic Publishers, 1994, D. G. Lowe, Object Recognition from local scale-invariant features, ICCV (International Conference on Computer Vision), 1999; J. Matas, J. Burianek, and J. Kittler. Object recognition using the invariant pixel-set signature, BMVC (British Machine Vision Conference), 2000; and F. Schaffalitzky and A. Zisserman. Viewpoint invariant texture matching and wide baseline stereo, ICCV, 2001, which are incorporated herein by reference.

Optionally, the image patches are acquired using one or more patch sampling strategies such as random sampling and/or grid sampling, optionally with spacings. Optionally, the size of a patch is of 9×9 pixels. Optionally, image patches along the border of the image are considered ignored. Optionally, the intensity values within an image patch are normalized to have zero mean and unit variance. This provides local contrast enhancement and augments the information within the image patches. Optionally, image patches that have a single intensity value of black are ignored.

According to some embodiments of the present invention, the data dimensionality and optionally the computational complexity of reducing the level of noise, may be diminished using a procedure such as a principal component analysis (PCA), principal component regression (PCR) and/or partial least squares (PLS) regression. For example data dimensionality of each 9×9 image patch is reduced in size from 81 to 7.

For example, when PCA is used, a resultant PCA component does not contain information regarding the average intensity of the respective image patch. This average value contains information that discriminates between the dark background and the bright tissue and may be used to distinguish between tissue types. In such embodiments, the mean gray level of the image patch may be taken as an additional multidimensional features feature.

Optionally, the center of each image patch, coordinates (x, y) is added to a respective image patch multidimensional record as two additional features, for example as an overall ten-dimensional image patch representation. The addition of the spatial coordinates to the image patch multidimensional record introduces spatial information into the image representation. Optionally, the relative feature weights in the proposed system are tuned experimentally on a test/cross-validation set, for example as described in the example below.

Optionally a dataset which documents the image patches is generated for each image in the training set. The dataset is optionally a multidimensional record.

Figures 4A, 4B, 4C:
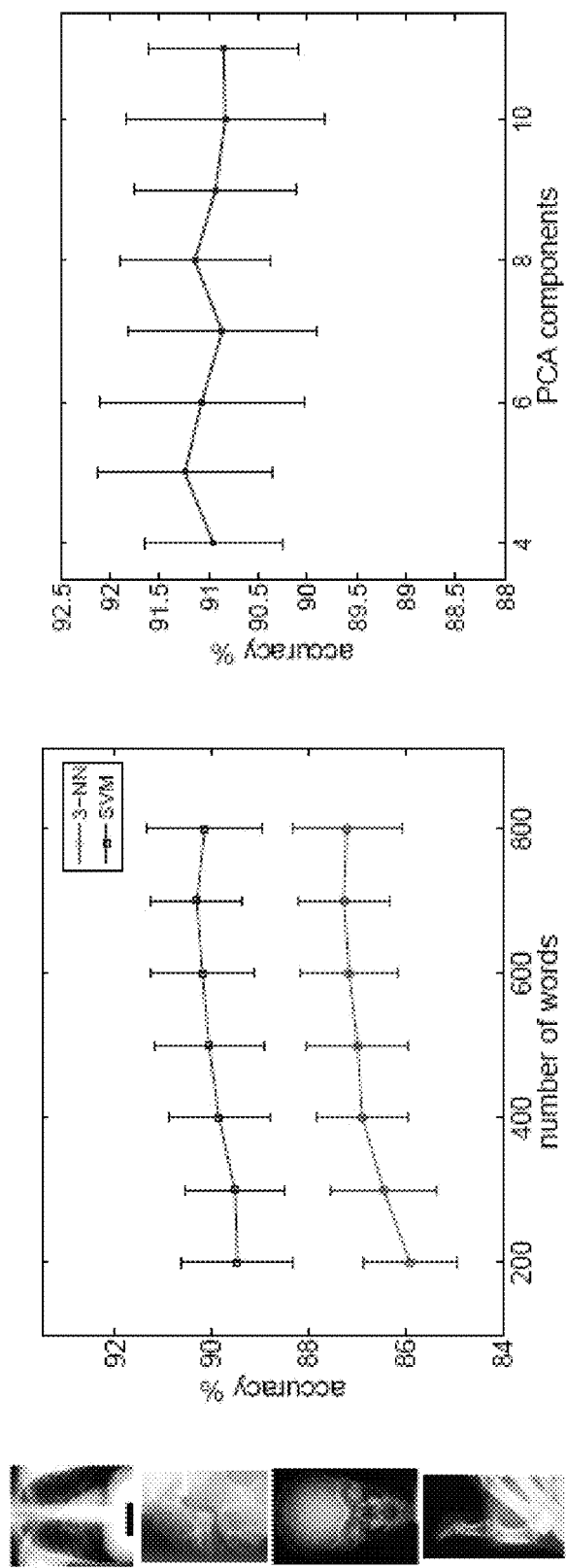

Now, as shown at 103, a dictionary is generated according to the image patches. First, some or all of the images are selected. Now, the image patches of the selected images are clustered in a plurality of clusters distributed in a feature space, which may be referred to herein as an image patch space. Each cluster is defined in a different subspace which may be referred to herein as visual word, for example using iterative square error partitioning and/or hierarchical technique. The visual words form an index or a codebook, referred to herein as a dictionary, of the image patches in a feature space. Optionally, the number of visual words is limited to a predefined amount. Optionally, the predefined amount is 700 or less, for example as shown in FIGS. 4B and 4C and described below. Optionally, each visual word includes 7 PCA coefficients, for example as described above.

Optionally, a k-means algorithm is used to cluster the image patches. This algorithm proceeds by iterated assignments of image patches to their closest cluster centers (visual word) and re-computation of the cluster centers (other visual words), see O. Duda, P. E. Hart, D. G. Stork, Pattern classification, John Wiley & Sons, 2000, which is incorporated herein by reference. Note that this dictionary development step is done in an unsupervised mode without any reference to the image categories, such as pathologies.

As shown at 104, each image is represented as a bag of visual words, namely a dataset of visual words which appears in the image, such as a visual word vector. The visual words are selected according to the image patches which have been identified in each image. The bag of visual words, which may be referred to herein as a visual-word vector, contains the presence and/or absence information of each visual word from the dictionary in the image, the count of each visual word (i.e., the number of image patches in the corresponding visual word cluster), or the count weighted by other factors. Optionally, the visual-word vector is represented as a histogram wherein each bin in the histogram is a visual word index number selected out of the dictionary and generated automatically from the data.

As shown at 105, the plurality of medical images, are categorized according to one or more pathologies which have been identified as depicted therein. The categorization is optionally performed manually, for example by a diagnosis of one or more, such as physicians, for example orthopedic physician and radiologists. Alternatively, the categorization may be performed automatically, for example using known image classification methods, and/or by an analysis of a diagnosis and/or a textual description that is attached to the image. Alternatively, the categorization may be semi automatic, for example by a combination of an automatic textual and/or image classification methods and a manual verification of one or more practitioners. Each visual-word vectors is categorized according to the image which is related thereto.

Now, as shown at 106, the categorized visual-word vectors of the categorized images are combined to create a category model.

Optionally, giving the categorized visual-word vectors, which may be divided to categories, a support vector machine (SVM) training algorithm builds a category model that allows estimating to which one of the categories, if any, a certain medical image which is not from the training set is related. Optionally, the category model is an SVM model in which the visual-word vectors are represented as points in space, mapped so that the categorized visual-word vectors of the separate categories are divided by a clear gap that is as wide as possible. Optionally, the SVM training algorithm is a multi-class SVM that is optionally implemented as a series of one-vs-one binary SVMs with a radial basis function (RBF) kernel, for example based on the LIBSVM library, found in http://www.csie.ntu.edu.tw/~cjlin/libsvm/, which is incorporated herein by reference. Optionally, SIFT image features are extracted from each image and used to reduce the visual word extraction time.

Now, the category model is outputted, as shown at 107, facilitating the categorization of new medical image which is mapped into the space of the category model and predicted to belong to a category based on which side of the gap they fall on.

Figure 2:
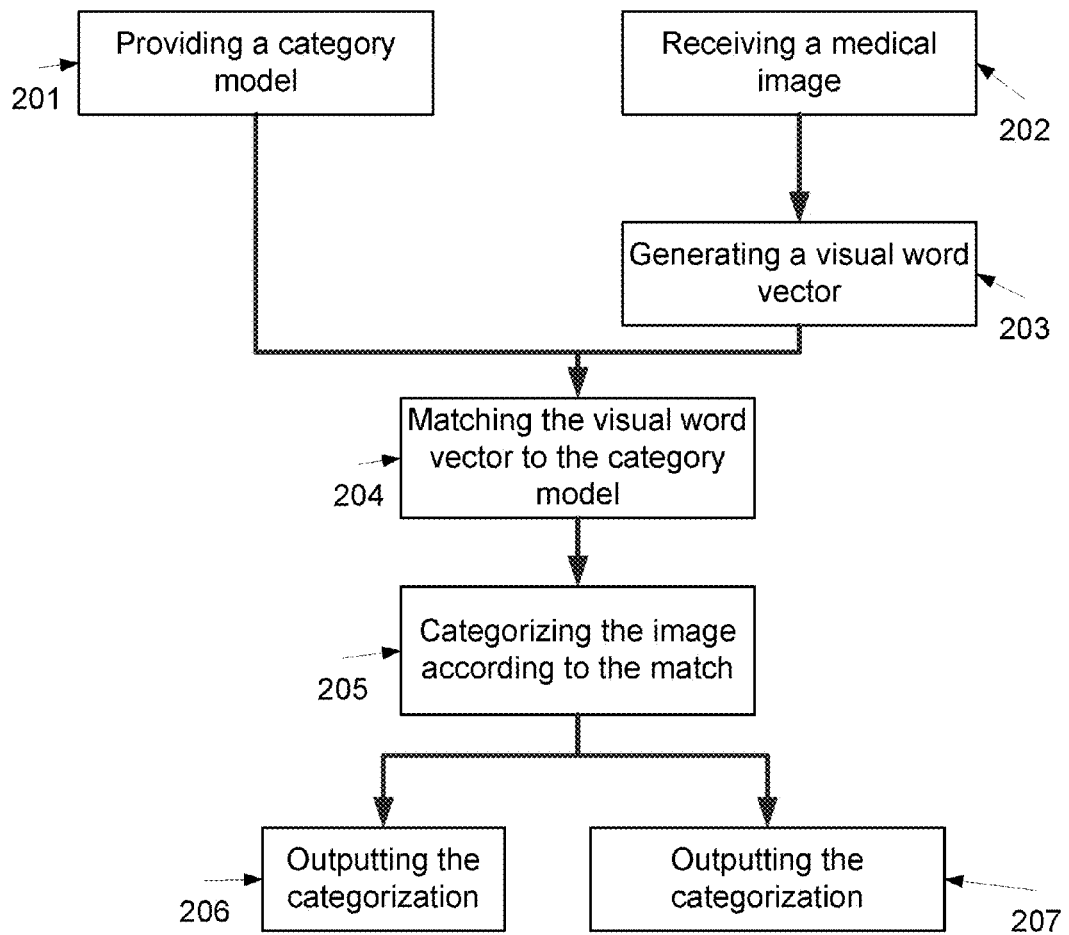

Reference is now made to FIG. 2, which is a method 200 of classifying a medical image using a category model, for example as generated according to FIG. 1, according to some embodiments of the present invention.

First, as shown at 201, a category model which maps a plurality of categorized visual-words and/or visual-word vectors in space is received. The category model is optionally generated based on a training set of a plurality of exemplary medical images, for example as depicted in FIG. 1.

As shown at 202, an examined medical image is received. Optionally, the examined medical image is uploaded from a PACS and/or a non transitory storage medium, such as a CD, a DVD, and/or a memory card, to a client terminal which implements the method 200 and/or a client terminal connected to a computing unit which implements the method 200. The client terminal may be a laptop, a Smartphone, a cellular phone, a tablet, a personal computer a personal digital assistance (PDA) and the like.

Now, as shown at 203, a visual word vector and/or a histogram are generated according to an analysis of the image. The visual word vector represents image patches of the image which correspond with visual words at the space of the category model. The conversion is optionally similar to the described in relation to blocks 102, 103, and 105 where image patches are identified and matched with visual words in the dictionary to generate the respective bag of visual words.

Now, as shown at 204, the visual words of the examined image are matched with the category model. The match maps the visual words of the vector in the space of the category model. The mapping is to a subspace, or to the proximity of a subspace, which is associated with a certain category mapped in the category model. This allow, as shown at 205, the categorization of the examined image. As shown at 206, the categorization is outputted, for example presented to the operator of the client terminal, forwarded to a database which hosts the examined image for an association therewith, and/or sent, for example via an email service, to a practitioner which is related to the examined image and/or to the imaged patient.

Optionally, each shown at 207, each examined image and/or the related visual word vector and the categorization thereof is used to update the category model. In such a manner, the category model is improved each time it is being used for categorizing a medical image. The update may be performed by rerunning the dictionary generation process and respectively the category model generation process depicted in blocks 103, 104, and 106 of FIG. 1.

It should be noted that the method depicted in FIG. 2 allows categorizing medical images such as 2 dimensional (2D) X-Ray images and 3D CT or MRI images without segmentation and/or registration. In such a manner, the computational complexity involved in categorizing each examined image is minimal. Such a method may be implemented on thin end client with limited computational power.

Figure 3:
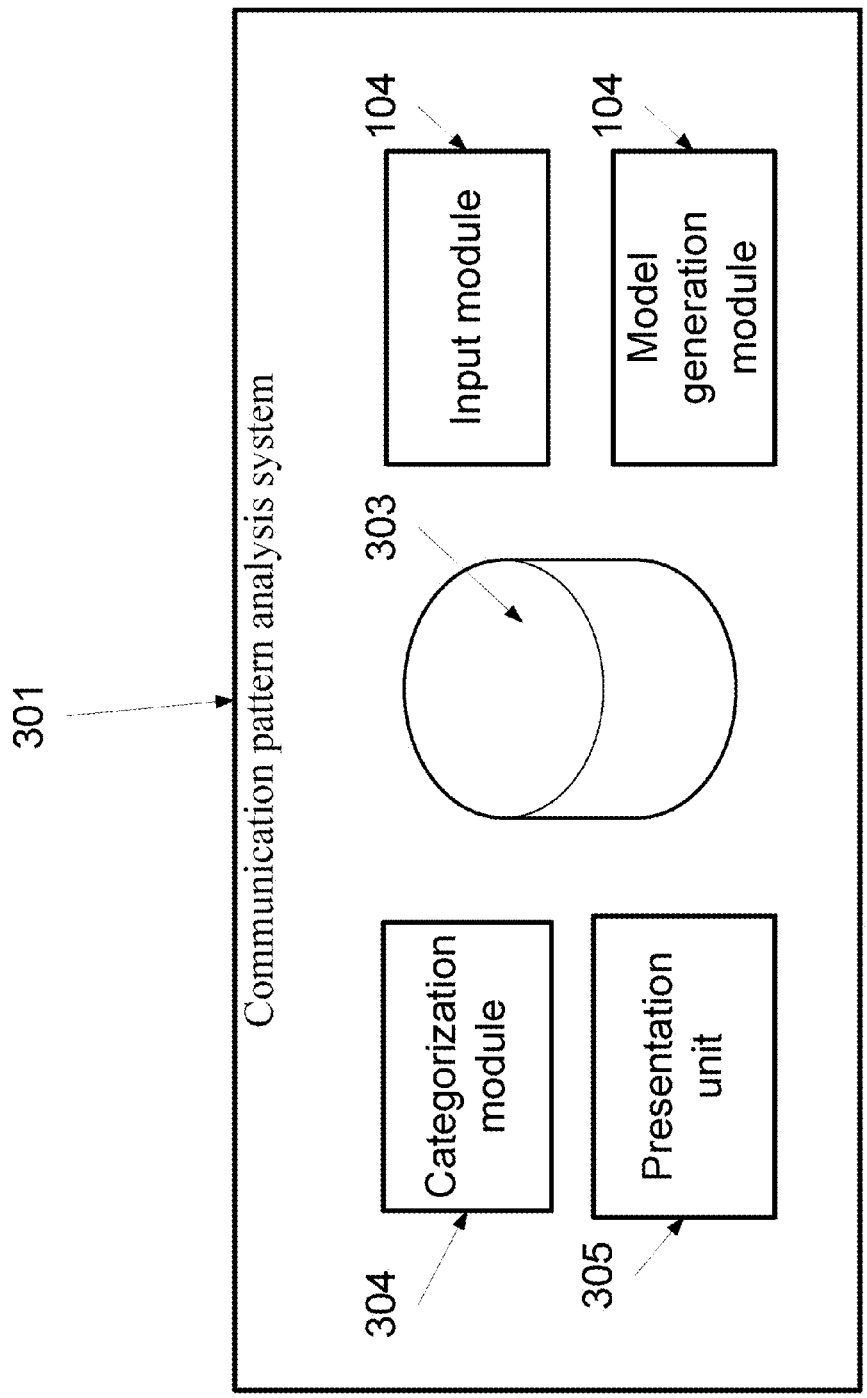

Reference is now made to FIG. 3, which is a schematic illustration of a medical image analysis system of classifying a medical image using a category model, for example as generated according to FIG. 1, according to some embodiments of the present invention. The medical image analysis system 301 comprises an input module 302 for obtaining or receiving a medical image, a repository 303 for storing the category model and a categorization module 304 for categorizing the received medical image according to the category model. The input module 302 is designed to receive the medical image either directly from a medical imaging system or indirectly via a content source such as a PACS server, a PACS workstation, a computer network, or a portable memory device such as a DVD, a CD, a memory card, etc. Each received medical image is preferably associated with medical information. Such medical information may comprise the patient age, gender, medical condition, ID, and the like. Optionally, the medical image found in a digital imaging and communications in medicine (DICOM) object.

Optionally, the input module 302 is to forward the received medical image to the categorization module 304. The categorization module 304 optionally implements the method depicted in FIG. 2 so as to categorize the received image. The system 301 further includes a presentation unit 305, such as a display for presenting the categorization performed by the categorization module 304. The categorization may be displayed in a window or any other graphical user interface (GUI). When such an embodiment is used, the medical image analysis system 301 can alert the user on real time whenever a critical pathological categorization has been identified in one of the received medical images. Such an embodiment increases the effectiveness of a therapy given to patients as it alarms the system user regarding a pathological indication immediately after the medical image has been acquired. Optionally, the medical image analysis system 301 includes a model generation model which is set to generate and optionally to update the category model, for example as described above in relation to FIG. 1 and block 207 of FIG. 2.

It is expected that during the life of a patent maturing from this application many relevant systems and methods will be developed and the scope of the term client terminal, computing unit, and image processing is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Reference is now made to the following example, which together with the above descriptions, illustrates some embodiments of the invention in a non limiting fashion.

In the example system and method validation was conducted using a database of 12,000 categorized medical images, radiographs. This dataset is the basis for the ImageClef 2007 medical image classification competition; see T. Deselaers et al. Overview of the imageclef 2007 object retrieval task, in workshop of the cross language evaluation forum 2007, volume 5152, 2008, which is incorporated herein by reference. A set of 11,000 medical images have been used for training, and 1000 serve for testing. There are 116 different categories within the archive, differing in either the examined region, the image orientation with respect to the body or the biological system under evaluation. Several of these images are presented in FIG. 4A. The distribution of the images across the categories is non-uniform; the most frequent category contains over 19% of the images in the database, while many categories are represented by less than 0.1% of the images. The system parameters have been optimized using the training portion of this set, by running 20 cross-validation experiments trained on 10,000 images and verified on 1000 randomly drawn test images. Each parameter was optimized independently. As FIG. 4B shows, increasing the number of dictionary words proved useful up to 700 words. Beyond this value the running time increased significantly, with no evident improvement in the classification rate. FIG. 4B also demonstrates that using an SVM classifying algorithm provides results that are more than 3% higher than the best K-NN classifier (k=3). The effect of the number of PCA components was examined next. FIG. 4C shows similar classification results in the range of 5 to 8 components, with an average classification rate of approximately 90% using the SVM classifying algorithm. Based on the above experiments, a dictionary size of 700 visual words was selected, where each word contains 7 PCA coefficients.

Incorporating spatial coordinates of the patch as additional features improves the classification performance noticeably, as seen in FIG. 5, which is a graph mapping the relation between the weight of spatial features in x-axis and the classification accuracy in y-axis where the bars show mean and standard deviation of 20 experiments.

The optimal range for the (x, y) coordinates is [−3; 3]. The patch variance normalization step improves the classification rate as well: with no normalization, the average classification rate is 88:19, while with normalization it climbs to 90:9. Using SIFT features with the SVM classification increased significantly the feature extraction time, and achieved an average of 85.4% classification accuracy, well below the classification rate of a raw patch based classification.

Using the parameter set defined above, classification of previously unseen 1000 test images was conducted. The overall classification rate achieved is 89:1%. The total running time for the whole system, training and classification, was approximately 40 minutes on the full resolution images, and 3 minutes on the ¼ scaled down images, as measured on dual quad-core Intel Xeon 2.33 GHz.

Reference is now also made to another example in which a system and a method validation were conducted using a database of 66,000 categorized medical images, radiographs. This dataset is optionally, the ImageClef 2008 database; see http://www.imageclef.org/ImageCLEF2008, which is incorporated herein by reference. In ImageClef 2008 a large-scale medical image retrieval competition was conducted. A database of over 66,000 images was used with 30 query topics. Each topic is composed of one or more example images and a short textual description in several languages. The objective is to return a ranked set of 1000 images from the complete database, sorted by their relevance to the presented queries. Sample queries from this challenge and the first few returned images are seen in FIG. 6 which depicts a set of images where the first two images are the query images and the following images (left to right, top to bottom) are the retrieval results. The retrieved results were manually judged for relevance by medical experts. FIG. 7 is a graph depicting the relation between the precision shown for first 5, 10, 15, 20 and 30 returned images and the number of images. The precision achieved using the method described above is marked with (*). The other outcomes are achieved using visual retrieval algorithms described in the Muller et al. Overview of the imageclefmed 2008 medical image retrieval task. In CLEF working notes (http://www.clef-campaign.org/2008/working_notes/CLEF2008WN-Contents.html.), which is incorporated herein by reference.

In this Figure, the line labeled 'Proposed System' depicts the outcomes achieved when using image patch normalization and the line labeled 'Not Normalized' depicts the outcomes achieved when using the patch original gray levels. The normalized patch approach in the proposed system is shown to rank first among the automatic purely visual retrieval systems.

The retrieval system is computationally efficient, with an average retrieval time of less than 400 ms per query.

Categorization on the Pathology Level

Image similarity-based categorization and retrieval becomes of clinical value once the task involves a diagnostic-level categorization, such as healthy vs. pathology. Optionally, the category models generated as described in the examples above were examined on chest x-rays obtained for various clinical indications in the emergency room of Sheba medical center. 102 frontal chest images have been used; from which 26 diagnosed as normal and 76 as having have one or more pathologies, such as lung infiltrates, left or right pleural effusion or an enlarged heart shadow. X-ray interpretations, made by two radiologists, served as the referral gold standard. Inconclusive results were not included in this set. Four sample images from this data are presented in FIG. 7. A patch-based classifying was implemented using an SVM classifying algorithm with two classes, the classification was conducted for each pathology type, and for healthy vs. any pathology. In order to preserve the generalization ability of the classifiers, system parameters were tuned using the general ImageClef 2007 database and were not specifically tuned to the lung pathology task. A leave one out classification was performed (results averaged over 102 trials). Table 1 summarizes the classification results:

|  | Normal images | Abnormal images | Sensitivity | Specificity |
| --- | --- | --- | --- | --- |
| Any Pathology | 22/26 | 74/76 | 94.8 | 91.7 |
| Enlarged heart | 20/23 | 43/44 | 95.3 | 93.5 |
| Lung Infiltrates | 23/33 | 27/34 | 76.7 | 73.0 |
| Right pleural effusion | 12/23 | 42/51 | 57.1 | 79.2 |
| Left pleural effusion | 15/27 | 38/47 | 62.5 | 76.0 |

The software identified correctly 74 out of 76 abnormal and 22 out of 26 normal x-rays with 4 false positives and 2 false negatives cases, resulting in a sensitivity of 94.87% and specificity of 91.67%. In the task of between-pathology discrimination, the performance depends on the pathology type: it is highly accurate in detecting enlarged hearts, with a sensitivity of 95.24% and specificity of 93.48%. It is less accurate in detecting lung infiltrates and effusions. Briefly stated, in this study a patch-based classification system was applied to a variety of medical image archives, in categorization and retrieval tasks. The exemplary system was tuned to achieve high accuracy, with an average of over 90% correct classification on a publicly available database of 12,000 medical radiographs. In the ImageClef 2008 medical annotation challenge it ranked second. It is a highly efficient, with less than 200 milliseconds training and classification time per image. Using the same methods, an image retrieval utility, which was ranked first in ImageClef 2008 among the visual retrieval systems was developed. Extending the system to pathology-level discrimination showed initial results for lung disease categorization.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of generating a category model for classifying medical images, comprising:
   providing a plurality of anatomical medical images imaging at least one internal organ or area of a body;
   in each of said plurality of anatomical medical images identifying a plurality of image patches, each image patch is represented by a plurality of repeatable multi-dimensional features in a pixel area of a respective anatomical medical image and image coordinates of said pixel area in said respective anatomical medical image, wherein said plurality of repeatable multidimensional features of each of the plurality of image patches comprises at least one noise reduction based coefficient and a gray level feature of the image patch;
   for each of said image patches, weighting at least some of the noise reduction based coefficient, the gray level feature, and the image coordinates, wherein said weighting is tuned experimentally on a cross-validation set;
   generating a plurality of visual words by clustering said plurality of image patches represented by said weighted at least one noise reduction based coefficient, gray level feature, and image coordinates of each one of said plurality of image patches;
   modeling a category model mapping a relation between said plurality of visual words;
   outputting said category model adapted to categorize a pathology in a new anatomical medical image based on a new set of image patches from said new anatomical medical image and the coordinates of pixel areas of said new set of image patches in said new anatomical medical image,
   wherein at least one of said providing, generating, modeling, and outputting is performed by at least one processor.

2. The method of claim 1, further comprising dividing said plurality of medical images among a plurality of categorized groups.

3. The method of claim 1, wherein an index of said plurality of visual words comprises less than 700 visual words.

4. The method of claim 1, wherein said plurality of medical images are part of a training set having more than 10,000 medical images.

5. The method of claim 1, wherein said generating comprises clustering a plurality of local descriptors based on repeatable multidimensional features in each image in a plurality of clusters, said plurality of visual words being defined according to said plurality of clusters.

6. The method of claim 5, wherein said clustering is performed according to a principal component analysis (PCA).

7. The method of claim 1, wherein said modeling is performed using a support vector machine (SVM) training procedure.

8. The method of claim 7, wherein said SVM training procedure is a multi-class SVM with a radial basis function (RBF) kernel.

9. The method of claim 1, wherein said plurality of medical images are provided from a picture archiving communication system (PACS).

10. The method of claim 1, wherein a plurality of categorized groups define a plurality of said pathologies.

11. The method of claim 1, further comprising automatically categorizing said plurality of medical images.

12. The method of claim 1, wherein the category model is updated upon each usage of the category model.

13. The method of claim 1, further comprising normalizing each image patch, wherein each normalized image patch is formed from a transformation of intensity values from a corresponding image patch, to render the image patch less variant to brightness, and to provide local contrast enhancement.

14. The method of claim 13, wherein said intensity values from the image patch are obtained from pixels of the image patch.

15. The method of claim 1, wherein said repeatable multi-dimensional features in each said image are from three dimensional images.

16. The method of claim 1, wherein said outputting comprises outputting said category model for facilitating the categorization of an image based on local descriptors thereof including said image from three dimensional images.

17. The method of claim 10, wherein the plurality of pathologies is selected from the group consisting of enlarged heart, lung infiltrates, right pleural effusion and left pleural effusion.

\* \* \* \* \*